United States Patent [19]

Bianchi et al.

[11] Patent Number: 4,473,583

[45] Date of Patent: Sep. 25, 1984

[54] COMPOSITIONS CONTAINING CERTAIN DERIVATIVES OF 4-PHENYL-4-OXOBUTEN-2-OIC ACID AND METHODS OF TREATMENT USING THEM

[75] Inventors: Mario Bianchi; Fernando Barzaghi, both of Milan, Italy

[73] Assignee: Roussel UCLAF, Romainville, France

[21] Appl. No.: 435,463

[22] Filed: Oct. 20, 1982

[30] Foreign Application Priority Data

Oct. 22, 1981 [IT] Italy .................. 49548 A/81

[51] Int. Cl.³ .................. A61K 31/205; A61K 31/20; A61K 31/19; A61K 31/235
[52] U.S. Cl. .................. 424/316; 424/317; 424/318; 424/308
[58] Field of Search .............. 424/308, 317, 316, 318

[56] References Cited

U.S. PATENT DOCUMENTS

| | | | |
|---|---|---|---|
| 2,532,579 | 12/1950 | Thomas .................. | 424/308 |
| 2,562,208 | 7/1951 | Papa et al. .................. | 424/308 |
| 2,795,554 | 6/1957 | Shumard .................. | 424/308 |
| 3,753,997 | 8/1973 | Ash et al. . | |
| 3,763,148 | 10/1973 | Ash et al. . | |
| 3,846,470 | 11/1974 | Rabbe et al. .................. | 260/465 E |
| 3,910,959 | 10/1975 | Vallet .................. | 260/340.5 |
| 3,940,404 | 2/1976 | Ash et al. . | |
| 3,940,487 | 2/1976 | La Croix et al. .................. | 424/282 |
| 3,953,463 | 4/1976 | Ash et al. . | |
| 4,017,517 | 4/1977 | Murata et al. .................. | 260/340.5 |

FOREIGN PATENT DOCUMENTS

| | | | |
|---|---|---|---|
| 1282644 | 11/1968 | Fed. Rep. of Germany . | |
| 2047806 | 4/1972 | Fed. Rep. of Germany . | |
| 2103749 | 8/1972 | Fed. Rep. of Germany . | |
| 2501834 | 7/1975 | Fed. Rep. of Germany . | |
| 1566212 | 5/1969 | France . | |
| 1566213 | 5/1969 | France . | |
| 2132354 | 12/1972 | France . | |
| 8495M | 7/1973 | France . | |
| 2270856 | 12/1975 | France . | |
| 55-36434 | 3/1980 | Japan . | |
| 591415 | 9/1975 | Switzerland . | |
| 588108 | 6/1947 | United Kingdom .................. | 424/317 |
| 1387733 | 3/1975 | United Kingdom .................. | 424/317 |

OTHER PUBLICATIONS

Child, Ralph G. et al., "Fenbufen, a New Anti-Inflammatory Analgesic: Synthesis and Structure—Activity Relationships of Analogs", *Journal of Pharmaceutical Sciences*, vol. 66, No. 4, Apr. 1977, pp. 466–476.

Markovac, A. et al., "Antimalarials. 3. 2,6-Bix(aryl)-4-pyridinemethanols with Trifluoromethyl Substituents", *Journal of Medicinal Chemistry*, vol. 15, No. 9, Sep. 1972, pp. 918–922.

Pettit, George R. et al., "Bufadienolides. 1. Introduction and Base-Catalyzed Condensation of Methyl Ketones with Glyoxylic Acid", *Journal of Organic Chemistry*, vol. 35, No. 5, May 1970, pp. 1367–1376.

Rice, Grace Potter, "The Isomeric Esters of Para-Ethoxy-Benzoylacrylic Acid", J.A.C.S., vol. 46, No. 10, Oct. 1924, pp. 2319–2326.

Journal of the American Chemical Society, vol. 71, No. 4, Apr. 1949, F. K. Kirchner et al., pp. 1210–1213.

Journal of the American Chemical Society, vol. 70, No. 10, Oct. 1948, D. Papa et al., pp. 3356–3360.

European Journal of Medical Chemistry Chimica Therapeutica, vol. 13, No. 3, May–Jun., 1978, H. Orzalesi et al., pp. 259–264.

Beilstein, vol. 19, p. 312.

European Journal of Medical Chemistry Chimica Therapeutica, vol. 12, Jan.–Feb. 1977, No. 4, pp. 17–20.

*Primary Examiner*—Frederick E. Waddell
*Attorney, Agent, or Firm*—Stevens, Davis, Miller & Mosher

[57] ABSTRACT

Pharmaceutical compositions including compounds of formula (I):

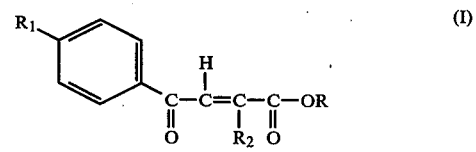

in which $R_1$ represents a hydrogen atom, a hydroxy radical or an alkyl radical containing from 1 to 8 carbon atoms, $R_2$ represents a hydrogen atom or an alkyl radical containing from 1 to 8 carbon atoms, and R represents a hydrogen atom or an alkyl radical containing from 1 to 8 carbon atoms, as well as the pharmaceutically acceptable alkali metal, alkaline earth metal, ammonium or amine salts of the products of formula I in which R represents a hydrogen atom. These compositions have been found to be useful in treating hyperchlorhydria, gastric and gastroduodenal ulcers, gastritis, hiatal hernias and gastric or gastroduodenal ailments accompanied by gastric hyperacidity.

19 Claims, No Drawings

COMPOSITIONS CONTAINING CERTAIN DERIVATIVES OF 4-PHENYL-4-OXOBUTEN-2-OIC ACID AND METHODS OF TREATMENT USING THEM

The present invention relates to pharmaceutical compositions containing certain derivatives of 4-phenyl-4-oxobuten-2-oic acid.

The object of the invention is compositions containing compounds of formula I:

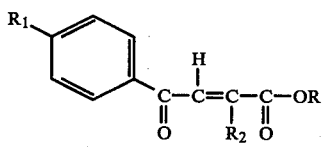

in which R represents a hydrogen atom or an alkyl radical containing from 1 to 8 carbon atoms, $R_1$ represents a hydrogen atom, a hydroxy radical or an alkyl radical containing from 1 to 8 carbon atoms, and $R_2$ represents a hydrogen atom or an alkyl radical containing from 1 to 8 carbon atoms, as well as the pharmaceutically acceptable alkali metal alkaline earth metal, ammonium or amine salts of the compounds of formula I in which R represents a hydrogen atom.

When $R_1$ represents an alkyl radical, it is preferably the methyl, ethyl, n-propyl, isopropyl, n-butyl, isobutyl or terbutyl radical.

When $R_2$ represents an alkyl radical, it is preferably the methyl radical.

When R represents an alkyl radical it is preferably the methyl, ethyl, n-propyl, isopropyl, n-butyl, isobutyl, terbutyl or n-pentyl radical.

The alkali metal or alkaline earth metal salts of the compounds of formula I when R represents a hydrogen atom are preferably the sodium, potassium, lithium or calcium salts.

The amine salts of the products of formula I in which R represents a hydrogen atom are the usual amine salts. Such amines are monoalkyl amines, such as methylamine, ethylamine and propylamine, dialkylamines, such as dimethylamine, diethylamineand di-n-propylamine, and trialkylamines such as triethylamine. Mention may also be made of piperidine, morpholine, piperazine and pyrrolidine.

The products of formula I may be present in the form of cis or trans geometric isomers and these different isomers, of course, fall within the scope of the invention.

The compounds of formula I and their salts have useful pharmacological properties and in particular substantial anti-ulcer activity in treating ailments of the digestive tract. Furthermore, when in contact with the gastric mucosa, they exhibit anti-gastric secretion and cytoprotective activities.

These properties make it possible to use the compositions of the invention in human or animal medicine, particularly in the treatment of hyperchlorhydria, gastric and gastroduodenal ulcers, gastritis, hiatal hernias or gastric and gastroduodenal ailments accompanied by gastric hyperacidity.

The doses, which varies in accordance with the product used and the ailment in question, may range for instance, between 0.05 g and 2 g/day for adults per os.

Among the compounds of formula (I), those in which R represents a hydrogen atom, as well as their pharmaceutically acceptable alkali metal, alkaline earth metal, ammonium or amine salts are preferred. Also preferred are compounds of the formula I in which $R_2$ represents a hydrogen atom, those in which $R_1$ represents a hydrogen atom, those in which $R_1$ represents a hydroxy radical in 4-position and those in which $R_1$ represents a methyl radical.

Among the preferred embodiments of the invention, particularly preferrable is (E) 4-phenyl-4-oxobuten-2-oic acid as well as its pharmaceutically acceptable alkali metal, alkaline earth metal, ammonium or amine salts. Also preferred are (Z) 4-phenyl-4-oxobuten-2oic acid and (E) 4-(4-hydroxyphenyl)-4-oxobuten-2-oic acid as well as their pharmaceutically acceptable alkali metal, alkaline earth metal, ammonium or amine salts.

As discussed previously, invention has as its object pharmaceutical compositions which contain at least one compound of the formula I as an active principle.

The compositions are prepared in a manner so that they can be administered by digestive (oral or rectal) or parenteral routes. The compositions may be solid or liquid and may be present in the pharmaceutical forms currently used in human or animal medicines such as, for instance, simple or coated tablets, capsules, granules, suppositories and injectable preparations. These are prepared by the usual methods.

The active principle or principles may be incorporated in excipients customarily used in these pharmaceutical compositions, such as talc, gum arabic, lactose, starch, magnesium stearate, cocoa butter, aqueous or non-aqueous vehicles, animal or vegetable fats, paraffin derivatives, gylcols, various wetting, dispersing or emulsifying agents and preservatives.

The compounds of formula I are products which are generally known. They may be prepared, for instance, by the methods described in J. Am. Chem. Soc. 70, 3356, Org. Synth. Coll., Vol. III, p. 109; J. Org. Chem. 13, 284 (1948) J. Am. Chem. Soc. 75, (1953) and J. Chem. Soc. 1953, 3669.

For example, the compounds of formula I can be prepared by condensation of glyoxylic acid with an acetophenone which is substituted on the phenyl ring, in the presence of acetic anhydride or another dehydrating agent. The examples set forth below indicate some of the methods which can be used for the preparation of the compounds of formula I.

The following examples illustrate the invention without, however, limiting it.

EXAMPLE 1

(E) 4-phenyl-4-oxobuten-2-oic acid 100 g of anhydrous $AlCl_3$ were added, with stirring, in the course of 20 minutes to 34 g of maleic anhydride which has been dissolved in 175 g of benzene. The solution was held under reflux for one hour and then cooled in an ice bath and hydrolyzed by first adding 200 cc of water and then 50 cc of concentrated HCl. Stirring was effected for 40 minutes and the benzene was then evaporated under vacuum. The remainder was cooled to 0.5° C., and a yellow solid was filtered off and washed with 100 cc of water and 25 cc of a concentrated solution of HCl. The solid was dissolved in 200 cc of water with 40 g of sodium carbonate, treated with activated charcoal and then acidifed very slowly with 70 cc of concentrated hydrochloric acid, while stirring vigorously and cooling in ice. The precipitate was filtered, washed with water and dried at 50° C. 51 g of a product were obtained (MP =92° C.) and later recrystalliz·d from benzene. This provided the desired compound, melting at 94–95° C. This product is described in Org. Synth. Coll. Vol. III, page 109.

EXAMPLE 2

4-tolyl-4-oxobuten-2-oic acid

Operating in the same manner as in Example 1, but starting with toluene and maleic anhydride, the desired compound, melting at 128°–134° C. was obtained. The compound is described in J. Am. Chem. Soc. 70, 3356 (1948).

EXAMPLE 3

(Z) 4-phenyl-4-oxobuten-2-oic acid 8 g of (E) 4-phenyl-4-oxobuten-2-oic acid were dissolved in 120 cc of benzene, the resultant solution being slightly warmed. The solution was placed in a Petri dish and exposed for two days to direct sunlight. Solvent was added three times because of the rapid evaporation. At the end of the second day, a solid residue remained, which was crystallized from 25 cc of benzene. It was filtered and dried at room temperature. 4 g of the desired product were obtained. This product is described in J. Org. Chem. 13, 284 (1948).

EXAMPLE 4

2-methyl-4-phenyl-4-oxobuten-2-oic acid 6 g of 2-methylene-4-phenyl-4-oxobuten acid were placed in suspension in 150 cc of ethyl ether and treated with 30 cc of triethylamine. Agitation was effected for four hours at room temperature and it was then set aside for 20 hours. The solvent was evaporated and the residue taken up by triturating it with 2 N hydrochloric acid. The resulting solid was filtered and crystallized from a (1:1) ethanol: water mixture. 3.4 g of the desired compound were obtained.

MP =103°–106° C. (Yield: 57%).

A sample was recrystallized from water.

MP =108°–110° C.

EXAMPLE 5 (E)

4-(4-hydroxyphenyl)-4-oxobuten-2-oic acid

A mixture of 3.7 g of glyoxylic acid monohydrate and 5.4 g of p.hydroxy acetophenone in 10 cc of acetic acid was heated for 20 hours at the boiling point. The reaction mixture was cooled, diluted with water and extracted with ethyl acetate. The organic phase was separated and dried and the solvent expelled. The residue was chromatographed over silica, eluting with a mixture of benzene, ethyl acetate and acetic acid (50:50:10). A product was obtained which was then purified by dissolving in an aqueous solution with 5% sodium bicarbonate, extracting the impurities with ethyl acetate, acidifying the aqueous phase with 2 N hydrochloric acid and extracting again with ethyl acetate. After evaporation of the solvent and treatment with activated charcoal in water and then drying, 2.7 g of the desired compound melting at 193°–195° C. were obtained.

PHARMACEUTICAL FORMS

EXAMPLE 6

Tablets

Tablets of the following formula were prepared:
product of Example 1: 100 mg
excipient q.s. for a finished tablet of: 300 mg
(details of the excipient: lactose, wheat starch, processed starch, rice starch, magnesium stearate, talc).

EXAMPLE 7

Capsules

Capsules of the following formula were prepared:
product of Example 1: 100 mg
excipient q.s. for a finished capsule of: 300 mg
(details of the excipient: talc, magnesium stearate, aerosil).

PHARMACOLOGICAL STUDY (1) Determination of the anti-gastric secretion activity The technique used is described by H. SHAY et al. in Gastroenterology 5, 43, 1945.

Male rats were used having a weight of about 200 g (10 animals per lot), and were kept without food for 48 hours but allowed a 8% gluclose solution ad libitum. After the rats were slightly anesthetized with ether, the pylorus of each was ligated. After the end of the operation, the product to be tested in different doses or, in the case of the control animals a solution of 0.5% carboxymethyl cellulose, was administered intraduodenally, after which the abdominal incision sutured.

Three hours later, the animals were sacrified and their stomachs removed after ligating the esophagus. The gastric juice was removed and centrifuged. The volume of gastric juice obtained was then determined and the total acidity of the gastric juice was obtained by titrating a 100 μl sample of gastric juice to a pH of 7 by means of 1/10 N sodium hydroxide solution.

The percentages of the variation of the total acidity of the gastric secretions, between test animals and control animals were calculated and are set forth in the table appearing below.

(2) Determination of the anti-ulcer activity Stress Ulcer

The technique consists of inducing stomach ulcers by stress in rats (stress and cold). The technique used is described by E. C. SENAY and R. J. LEVINE, Proc. Soc. Exp. Biol. 124, 1221 (1967).

Female rats of 150 g (5 animals per lot) were used which has been fasting for 48 hours with water ad libitum and glucose solution for 8 hours. Through an esophageal tube, the animals received a test compound, or a solution of 0.5% carboxy methyl cellulose in the case of the control animals. Two hours later, the animals were bundled in a jacket of netting. Their paws were bound and the entire unit was placed in a refrigerator at 8° C. for two hours. The rats were freed and killed by ether.

Their stomachs were removed, opened along the greater curvature and examined with a binocular magnifier. The seriousness of the lesions was graded from 1 to 3 for each stomach.

For each lot of rats, the average intensity of the ulcerations was calculated. The degree of ulceration for test animals was compared with the control animals for each lot. The results are set forth in the table appearing below.

(3) Determination of the Acute Toxicity

The $LD_{50}$ was evaluated after the administration of the products orally to mice.

RESULTS
Anti-secretion and anti-ulcer activity (% variation as compared With the controls)

| Product of example | LD$_{50}$ mg/kg | Dose mg/kg | Acid Concentration | Ulceration |
|---|---|---|---|---|
| 1 | 250 | 10 | −66 | −54 |
| 2 | 250 | 10 | −61 | −39 |
| 3 | 370 | 10 | −81 | −93 |

What is claimed is:

1. A method of treating a patient suffering from hyperchlorhydria, gastric or gastroduodenal ulcers, gastritis, hiatal hernias, or gastric or gastroduodenal ailments accompanied by gastric hyperacidity, comprising:
administering to said patient a therapeutically effective amount of a compound of formula (I):

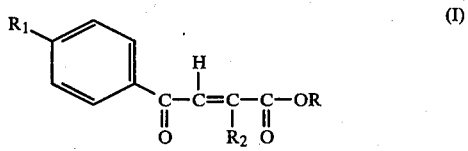 (I)

in which $R_1$ represents a hydrogen atom, a hydroxy radical or an alkyl radical containing from 1 to 8 carbon atoms, $R_2$ represents a hydrogen atom or an alkyl radical containing from 1 to 8 carbon atoms, and R represents a hydrogen atom or an alkyl radical containing from 1 to 8 carbon atoms or a pharmaceutically acceptable alkali metal, alkaline earth metal, ammonium or amine salt of a compound of formula (I) wherein R represents a hydrogen atom.

2. A method as claimed in claim 1 comprising administering a cytoprotectively and anti-gastric secretionary effective amount of a compound of formula (I) wherein R represents a hydrogen atom, or of a pharmaceutically acceptable alkali metal, alkaline earth metal, ammonium or amine salt of a compound of formula (I) wherein R represents a hydrogen atom.

3. A method as claimed in claim 1, wherein $R_2$ represents a hydrogen atom.

4. A method as claimed in claim 2, wherein $R_2$ represents a hydrogen atom.

5. A method as claimed in claim 1, wherein $R_1$ represents a hydrogen atom.

6. A method as claimed in claim 2, wherein $R_1$ represents a hydrogen atom.

7. A method as claimed in claim 3, wherein $R_1$ represents a hydrogen atom.

8. A method as claimed in claim 4, wherein $R_1$ represents a hydrogen atom.

9. A method as claimed in claim 1, wherein $R_1$ represents a hydroxy radical.

10. A method as claimed in claim 2, wherein $R_1$ represents a hydroxy radical.

11. A method as claimed in claim 3, wherein $R_1$ represents a hydroxy radical.

12. A method as claimed in claim 4, wherein $R_1$ represents a hydroxy radical.

13. A method as claimed in claim 1, wherein $R_1$ represents a methyl radical.

14. A method as claimed in claim 2, wherein $R_1$ represents a methyl radical.

15. A method as claimed in claim 3, wherein $R_1$ represents a methyl radical.

16. A method as claimed in claim 4, wherein $R_1$ represents a methyl radical.

17. A method as claimed in claim 1, wherein the compound of formula (I) is (E) 4-phenyl-4-oxobuten-2-oic acid or a pharmaceutically acceptable alkali metal, alkaline earth metal, ammonium or amine salt thereof.

18. A method as claimed in claim 1, wherein said compound is administered by digestive route.

19. A method as claimed in claim 1, wherein said compound is administered parenterally.

* * * * *